(12) United States Patent
Osawa

(10) Patent No.: US 10,734,107 B2
(45) Date of Patent: Aug. 4, 2020

(54) IMAGE SEARCH DEVICE, IMAGE SEARCH METHOD, AND IMAGE SEARCH PROGRAM

(71) Applicant: FUJIFILM Corporation, Tokyo (JP)

(72) Inventor: Akira Osawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

(21) Appl. No.: 16/172,012

(22) Filed: Oct. 26, 2018

(65) Prior Publication Data

US 2019/0131012 A1 May 2, 2019

(30) Foreign Application Priority Data

Oct. 31, 2017 (JP) .................................. 2017-210165

(51) Int. Cl.
*G06K 9/62* (2006.01)
*G16H 30/40* (2018.01)
(Continued)

(52) U.S. Cl.
CPC ............. *G16H 30/40* (2018.01); *G06F 16/51* (2019.01); *G06F 16/5838* (2019.01);
(Continued)

(58) Field of Classification Search
CPC ..................... G06T 7/0012; G06T 7/11; G06T 2207/30096; G06T 2207/30068;
(Continued)

(56) References Cited

U.S. PATENT DOCUMENTS

2014/0033126 A1\* 1/2014 Kreeger .................. G06T 15/08
715/821
2015/0262014 A1 9/2015 Iwamura et al.
(Continued)

FOREIGN PATENT DOCUMENTS

JP 2015-187845 A 10/2015
JP 2015-191285 A 11/2015

OTHER PUBLICATIONS

Depeursinge et al., "Case-based lung image categorization and retrieval for interstitial lung diseases: clinical workflows", Int J CARS, 2012, vol. 7, pp. 97-110.
(Continued)

*Primary Examiner* — Quan M Hua
(74) *Attorney, Agent, or Firm* — Birch, Stewart, Kolasch & Birch, LLP

(57) ABSTRACT

A finding classification unit classifies a target region included in an examination image into a plurality of lesion regions indicating a plurality of findings to generate a finding classification result. A first search unit searches for a case image similar to an examination image as a first similar case image from a case database DB based on the finding classification result. A display controller displays the examination image and the first similar case image. A key finding specification unit receives designation of a position of a key finding to the displayed examination image to specify a position of the key finding and specifies a finding name of the key finding having the position specified. A second search unit further searches for a case image associated with the specified position and the finding name of the key finding from the first similar case image to acquire a second similar case image.

8 Claims, 12 Drawing Sheets

(51) Int. Cl.
*G06F 16/583* (2019.01)
*G06F 16/51* (2019.01)
*G06T 7/00* (2017.01)

(52) U.S. Cl.
CPC .......... *G06K 9/627* (2013.01); *G06K 9/6215* (2013.01); *G06T 7/0012* (2013.01); *G06T 2207/10072* (2013.01); *G06T 2207/20081* (2013.01); *G06T 2207/20084* (2013.01); *G06T 2207/30061* (2013.01); *G06T 2207/30096* (2013.01)

(58) Field of Classification Search
CPC . G06T 2207/10072; G06T 2207/20081; G06T 2207/20076; G06T 2207/20101; G06T 7/143; G06T 2200/04; G06T 2207/10116; G01S 15/899; G01S 15/8993; G01S 7/52039; G01S 7/52042; G01S 15/894; G01S 7/52071; G06K 2209/05; G06K 9/4638; G06K 2209/051; G06K 9/00147; G06K 9/00456; G06K 2209/15; G06K 9/00442; G06K 9/00449; G06K 9/34; G06K 9/346; G06K 9/4652; G06K 9/623; G06K 9/00127; G06K 9/325; G06K 9/342; G06K 9/4671; G06K 9/6232; G06K 3/0454; G06N 5/022; G06N 20/00
See application file for complete search history.

(56) References Cited

U.S. PATENT DOCUMENTS

| | | | |
|---|---|---|---|
| 2016/0155225 A1* | 6/2016 | Madabhushi | G06T 7/0012 382/131 |
| 2017/0011199 A1 | 1/2017 | Oosawa | |
| 2018/0008237 A1* | 1/2018 | Venkataraman | A61B 8/06 |

OTHER PUBLICATIONS

Iwasawa, "Quantitative evaluation of CT image of interstitial pneumonia", Journal of Japanese Associations of Tomography, Aug. 2014, vol. 41, No. 2, Total No. pp. 11.

Jacob et al., "Evaluation of computer-based computer tomography stratification against outcome models in connective tissue disease-related interstitial lung disease: a patient outcome study", BMC Medicine, 2016, vol. 4, pp. 1-13.

* cited by examiner

FIG. 5

LUT1

| DIAGNOSIS NAME | FINDING NAME OF KEY FINDING |
|---|---|
| · PULMONARY INVOLVEMENT OF COLLAGEN VASCULAR DISEASE (1) RA | TIB, BRONCHIECTASIS, TRACTION BRONCHIECTASIS, FROSTED GLASS SHADOW, HONEYCOMB LUNG |
| · PULMONARY INVOLVEMENT OF COLLAGEN VASCULAR DISEASE (2) SSc (PSS) | BRONCHIECTASIS, TRACTION BRONCHIECTASIS, FROSTED GLASS SHADOW |
| · IDIOPATHIC INTERSTITIAL PNEUMONIA COP/OP | CONSOLIDATION, AIRBRONCHOGRAM, TRACTION BRONCHIECTASIS, FROSTED GLASS SHADOW |
| · IDIOPATHIC INTERSTITIAL PNEUMONIA UPPER LOBE-PREDOMINANT PULMONARY FIBROSIS (IDIOPATHIC PULMONARY UPPER LOBE FIBROSIS) | CONSOLIDATION, AIRBRONCHOGRAM, TRACTION BRONCHIECTASIS, FROSTED GLASS SHADOW, INTERLOBULAR SEPTAL THICKENING |
| · SARCOIDOSIS: PULMONARY LESION ONLY | NODULAR SHADOW, FROSTED GLASS SHADOW, INTERLOBULAR SEPTAL THICKENING, BRONCHOVASCULAR BUNDLE, FROSTED GLASS SHADOW |
| · UNCLASSIFIABLE INTERSTITIAL PNEUMONIA | TRACTION BRONCHIECTASIS, FROSTED GLASS SHADOW, INTERLOBULAR SEPTAL THICKENING, HONEYCOMB LUNG |
| · IPF ACUTE EXACERBATION | TRACTION BRONCHIECTASIS, FROSTED GLASS SHADOW, INTERLOBULAR SEPTAL THICKENING, HONEYCOMB LUNG |
| · HYPERSENSITIVITY PNEUMONITIS (1) SUMMER TYPE | CENTRILOBULAR FROSTED GLASS SHADOW |
| · HYPERSENSITIVITY PNEUMONITIS (2) BIRD-RELATED (INCLUDING CHRONIC TYPE) | CENTRILOBULAR FROSTED GLASS SHADOW |
| · DIP/DIP | FROSTED GLASS SHADOW |
| · CHRONIC NECROTIZING PULMONARY ASPERGILLOSIS (CNPA) | CONSOLIDATION, CAVITY, AIRBRONCHOGRAM, BRONCHIECTASIS |
| · NONTUBERCULOUS MYCOBACTERIOSIS (2) *M. intracellulare* | CONSOLIDATION, CAVITY, INTERLOBULAR SEPTAL THICKENING, BRONCHIECTASIS |
| · PSEUDOMONAS PNEUMONIA | CONSOLIDATION, CAVITY, BRONCHIECTASIS, TIB |
| · PULMONARY MUCORMYCOSIS | CONSOLIDATION, CAVITY, BRONCHIECTASIS |
| · IPF/UIP | TRACTION BRONCHIECTASIS, FROSTED GLASS SHADOW, INTERLOBULAR SEPTAL THICKENING, HONEYCOMB LUNG |
| ...... | ...... |

FIG.7

| CASE IMAGE FILE NAME | FINDING CLASSIFICATION RESULT | FILE NAME OF LABELED CASE IMAGE | KEY FINDING POSITION | FINDING NAME |
|---|---|---|---|---|
| IMG0001.dcm | ... | IMG0001_L.dcm | (x1, y1, z1) | TIB, BRONCHIECTASIS, TRACTION BRONCHIECTASIS, FROSTED GLASS SHADOW, HONEYCOMB LUNG |
| IMG0002.dcm | ... | IMG0002_L.dcm | (x2, y2, z2) | FROSTED GLASS SHADOW |
| IMG0003.dcm | ... | IMG0003_L.dcm | (x3, y3, z3) | TIB, BRONCHIECTASIS, TRACTION BRONCHIECTASIS, FROSTED GLASS SHADOW, HONEYCOMB LUNG |

DB $p1 = 0.10$
$p2 = 0.77$
...
$p32 = 0.52$
$p33 = 0.23$

| CASE IMAGE | WEIGHTED TOTAL |
|---|---|
| IMG0012.dcm | 10.2 |
| IMG0254.dcm | 10.1 |
| IMG0123.dcm | 9.8 |
| IMG0022.dcm | 9.6 |

FIG. 14

| CASE IMAGE FILE NAME | FINDING CLASSIFICATION RESULT | FILE NAME OF LABELED CASE IMAGE | FILE NAME OF KEY SLICE IMAGE | KEY FINDING POSITION | FINDING NAME |
|---|---|---|---|---|---|
| IMG0001.dcm | ... | IMG0001_L.dcm | IMG0001_010.dcm | (x1, y1, z1) | TIB, BRONCHIECTASIS, TRACTION BRONCHIECTASIS, FROSTED GLASS SHADOW, HONEYCOMB LUNG |
| IMG0002.dcm | ... | IMG0002_L.dcm | IMG0002_032.dcm | (x2, y2, z2) | FROSTED GLASS SHADOW |
| IMG0003.dcm | ... | IMG0003_L.dcm | IMG0003_007.dcm | (x3, y3, z3) | TIB, BRONCHIECTASIS, TRACTION BRONCHIECTASIS, FROSTED GLASS SHADOW, HONEYCOMB LUNG |

DB $p1 = 0.10$
$p2 = 0.77$
...
$p32 = 0.52$
$p33 = 0.23$

IMAGE SEARCH DEVICE, IMAGE SEARCH METHOD, AND IMAGE SEARCH PROGRAM

CROSS REFERENCE TO RELATED APPLICATIONS

The present application claims priority under 35 U.S.C. § 119 to Japanese Patent Application No. 2017-210165 filed on Oct. 31, 2017. The above application is hereby expressly incorporated by reference, in its entirety, into the present application.

BACKGROUND

Technical Field

The present invention relates to an image search device, an image search method, and an image search program that search for a case image similar to an examination image to be an examination target from a case database, in which a plurality of cases including one or more case images are registered.

Related Art

In recent years, with the advance of medical equipment, such as a computed tomography (CT) device and a magnetic resonance imaging (MRI) device, high-resolution three-dimensional images with higher quality are used in image diagnosis.

In a medical field, a similar case search device that searches for a past case similar to an examination image based on the examination image to be an examination target is known (for example, see Case-based lung image categorization and retrieval For interstitial lung diseases: clinical workflow, Adrien Depeursinge et al., Int J CARS (2012) 7:97-110, Published online: 1 Jun. 2011, JP2015-191285A, and JP2015-187845A). The examination image is, for example, a three-dimensional image acquired with a CT device, and is used for performing diagnosis of a patient, such as specification of a disease of the patient. Here, in a single examination using the CT device, a plurality of slice images are acquired. For this reason, an examination image having one or more slice images (referred to as examination slice images) is included in single examination data. Since a case is often created by integration of past examination data, a case image having one or more slice images (hereinafter, referred to as case slice images) is also included in data of a single case.

In Case-based lung image categorization and retrieval For interstitial lung diseases: clinical workflow, Adrien Depeursinge et al., Int J CARS (2012) 7:97-110, Published online: 1 Jun. 2011, a method has been suggested that classifies a case image of a lung into a plurality of lesion regions respectively indicating a plurality of findings and then registers the case image in a case database, classifies a lung into a plurality of lesion regions respectively indicating a plurality of findings on an examination image, and searches for a case image similar to the examination image based on a classification result of the findings on the examination image.

In JP2015-191285A, a method has been suggested that receives designation of a plurality of regions of interest each including one or more different target lesions in an examination image, acquires a feature quantity of each region of interest, compares the feature quantity of each region of interest with a feature quantity of a case lesion registered in a case database as a lesion in a case image to calculate an individual similarity of each region of interest, calculates an integral similarity based on a plurality of calculated individual similarities, and searches for a similar case similar to the examination image based on the integral similarity.

In JP2015-187845A, a method has been suggested that selects one or a plurality of images as a key image from among a plurality of images constituting a medical image, detects a position of a characteristic local structure of a human body from the medical image, specifies a local structure in the key image or in the periphery of the key image, generates information regarding the specified local structure as first local structure information, displays the first local structure information as a candidate to be described in an input field of a finding, and searches for an image interpretation report for reference of a new image interpretation report from a plurality of image interpretation reports stored based on the first local structure information of the new image interpretation report being currently created.

On the other hand, an interstitial pneumonia is known as a lung disease. A method has been suggested that analyzes a CT image of a patient with an interstitial pneumonia to classify and quantify a lesion indicating a specific finding, such as a honeycomb lung, a reticular shadow, and a cyst, included in the CT image (see Evaluation of computer-based computer tomography stratification against outcome models in connective tissue disease-related interstitial lung disease: a patient outcome study, Joseph Jacobi et al., BMC Medicine (2016) 14:190, DOI 10.1186/s12916-016-0739-7, and Quantitative evaluation of CT image of interstitial pneumonia, IWASAWA Tae, Journal of Japanese Associations of Tomography, Vol. 41, No. 2, August, 2014). In this way, the CT image is analyzed to classify and quantify a lesion, whereby it is possible to easily determine the degree of lung disease. The regions classified and quantified in this way are displayed in different colors respectively assigned thereto, whereby it is possible to easily diagnose how much a region of a specific symptom is included in an image.

In order to extract a structure, such as an organ to be noticed, from a three-dimensional image, such as a CT image, it is necessary to detect the structure in the three-dimensional image. Here, a method of deep learning has been suggested in order to classify pixels to be noticed in an image into a plurality of classes. Deep learning is a method of machine learning using a multilayer neural network constructed by hierarchical connection of a plurality of processing layers.

In deep learning, arithmetic processing is performed on a plurality of different pieces of arithmetic result data obtained with respect to input data by a previous hierarchical layer, that is, extraction result data of the feature quantity in each layer of the multilayer neural network. Then, additional arithmetic processing is performed on data of the feature quantity obtained in this way in subsequent processing layers, whereby it is possible to classify input data into a plurality of classes by improving a recognition rate of a feature quantity.

It is considered that such a method of deep learning is applied to the above-described three-dimensional image to classify pixels of a three-dimensional image into a plurality of classes. For example, in a case of a plurality of structures included in the three-dimensional image are classified, deep learning is performed on a neural network with the three-dimensional image as input such that a pixel to be a processing target in the three-dimensional image is classified into any one of a plurality of structures. With the use of the neural network subjected to deep learning in this way, it is possible to classify a target pixel of the input three-dimensional image into any one of a plurality of structure.

With the use of the method described in Case-based lung image categorization and retrieval For interstitial lung diseases: clinical workflow, Adrien Depeursinge et al., Int J CARS (2012) 7:97-110, Published online: 1 Jun. 2011, it is possible to search for a case image similar to a lesion included in the lung of the examination image. However, in the method described in Case-based lung image categorization and retrieval For interstitial lung diseases: clinical workflow, Adrien Depeursinge et al., Int J CARS (2012) 7:97-110, Published online: 1 Jun. 2011, a search is not performed based on a characteristic finding (hereinafter, referred to as a key finding) after a diagnosis name is specified. In the method described in JP2015-191285A, in a case where a region of interest is designated so as to surround a lesion indicating a key finding, it is possible to perform a search based on the key finding. However, in a case where another lesion other than the lesion indicating the key finding is included in the region of interest, it is not possible to perform a search based on the key finding with high accuracy. Furthermore, a search result may be considerably different with a difference in a way of surrounding the region of interest. In addition, in the method described in JP2015-187845A, a local structure is specified from a selected key image. For this reason, in a case where a physician has not stored a key image, it is not possible to specify a key finding.

SUMMARY

The invention has been accomplished in consideration of the above-described situation, and an object of the invention is to appropriately search a case image similar to an examination image based on a key finding designated on the examination image.

An image search device according to the invention comprises a finding classification unit that classifies a target region included in an examination image having one or more examination slice images into a plurality of lesion regions respectively indicating a plurality of findings to generate a finding classification result, a first search unit that searches for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image, a display controller that displays at least one of the one or more examination slice images or the examination image on a display unit, a key finding specification unit that receives designation of a position of a key finding to at least one of the displayed one or more examination slice images or examination image to specify a position of the key finding and specifies a finding name of the key finding having the position specified, and a second search unit that further searches for at least one of one or more case slice images or a case image associated with the specified position and finding name of the key finding from the first similar case image to acquire a second similar case image.

The "lesion region" means a region having a specific symptom or a specific form within the target region. For this reason, in the embodiment, it is assumed that a region of a structure itself having a specific form, such as a heart and a diaphragm is also included in the lesion region. Note that a finding of a physician to each of a plurality of lesion regions is obtained. For this reason, each of a plurality of lesion regions shows a finding.

The image search device according to the invention may further comprise a diagnosis name acquisition unit that acquires a diagnosis name of a registration target image having one or more registration target slice images to be registered in the case database, a registration key finding specification unit that, with reference to a table in which a variety of diagnosis names are associated with finding names of key findings corresponding to the variety of diagnosis names, specifies a finding name of a key finding of the registration target image based on the diagnosis name of the registration target image and the finding classification result in the registration target image and specifies a position of the key finding specified in the registration target image based on the specified finding name of the key finding, and a registration unit that registers the registration target image as a new case image in the case database in association with the finding classification result on the registration target image and the specified position and finding name of the key finding.

The image search device according to the invention may further comprise a key image acquisition unit that acquires a key registration target slice image from a registration target image having one or more registration target slice images to be registered in the case database, a registration key finding specification unit that specifies the finding name and the position of the key finding of the examination image based on the finding classification result in the key registration target slice image, and a registration unit that registers the registration target image as a new case image in the case database in association with the finding classification result on the registration target image and the specified position and finding name of the key finding.

The image search device according to the invention may further comprise a diagnosis name acquisition unit that acquires a diagnosis name of a registration target image having one or more registration target slice images to be registered in the case database, a first registration key finding specification unit that, with reference to a table in which a variety of diagnosis names are associated with finding names of key findings corresponding to the variety of diagnosis names, specifies a finding name of a key finding of the registration target image based on the diagnosis name of the registration target image and specifies a position of the key finding specified in the registration target image based on the specified finding name of the key finding and the finding classification result in the registration target image, a first registration unit that registers the registration target image as a new case image in the case database in association with the finding classification result on the registration target image and the specified position and finding name of the key finding, a key image acquisition unit that acquires a key registration target slice image from the registration target image, a second registration key finding specification unit that specifies the finding name and the position of the key finding of the examination image based on the finding classification result in the key registration target slice image, and a second registration unit that registers the registration target image as a new case image in the case database in association with the finding classification result on the registration target image and the specified position and finding name of the key finding.

The "registration target image" is an image to be registered in the case database, and the examination image may become the registration target image. In this case, the registration key finding specification unit can also be used as the key finding specification unit.

In the image search device according to the invention, the target region included in the case image may be divided into a plurality of subregions, a feature quantity relating to the lesion region may be calculated on each of the plurality of subregions, the feature quantity may be registered in the case database in association with the case image, and the first search unit may divide the target region included in the examination image into a plurality of subregions corresponding to the subregions of the case image, may calculate a feature quantity relating to the lesion region on each of the plurality of subregions, and may search for the first similar case image from the case database based on a weighted sum of similarities of the feature quantities between the subregions of the examination image and the case image registered in the case database.

In the image search device according to the invention, the finding classification unit may have a discriminator subjected to deep learning so as to classify the plurality of findings, and may classify the target region into the plurality of findings with the discriminator.

An image search method according to the invention comprises classifying a target region included in an examination image having one or more examination slice images into a plurality of lesion regions respectively indicating a plurality of findings to generate a finding classification result, searching for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image, displaying at least one of the one or more examination slice images or the examination image on a display unit, receiving designation of a position of a key finding to at least one of the displayed one or more examination slice images or examination image to specify a position of the key finding and specifies a finding name of the key finding having the position specified, and further searching for at least one of one or more case slice images or a case image associated with the specified position and finding name of the key finding from the first similar case image to acquire a second similar case image.

Note that a program causing a computer to execute the image search method according to the invention may be provided.

Another image search device according to the invention comprises a memory configured to store a command to be executed on a computer, and a processor configured to execute the stored command. The processor executes processing for classifying a target region included in an examination image having one or more examination slice images into a plurality of lesion regions respectively indicating a plurality of findings to generate a finding classification result, searching for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image, displaying at least one of the one or more examination slice images or the examination image on a display unit, receiving designation of a position of a key finding to at least one of the displayed one or more examination slice images or examination image to specify a position of the key finding and specifies a finding name of the key finding having the position specified, and further searching for at least one of one or more case slice images or a case image associated with the specified position and finding name of the key finding from the first similar case image to acquire a second similar case image.

According to the invention, the target region included in the examination image having one or more examination slice images is classified into a plurality of lesion regions respectively indicating a plurality of findings and the finding classification result is generated. Then, a case image similar to the examination image is searched as the first similar case image from the case database based on the finding classification result of the examination image, and at least one of one or more examination slice images or the examination image is displayed on the display unit. Then, the designation of the position of the key finding to at least one of the displayed one or more examination slice images or examination image is received, the position of the key finding is specified, and the finding name of the key finding having the position specified is specified. In addition, at least one of one or more case slice image or the case image associated with the specified position and finding name of the key finding is further searched from the first similar case image, and the second similar case image is acquired. For this reason, it is possible to appropriately search for a case image similar to an examination image based on a key finding designated to the examination image.

BRIEF DESCRIPTION OF THE DRAWINGS

FIG. 5 is a diagram showing a table in which a variety of diagnosis names are associated with finding names of key findings corresponding to a variety of diagnosis names.

FIG. 7 is a diagram showing a case database.

FIG. 14 is a diagram showing a case database.

DETAILED DESCRIPTION

Figure 1:
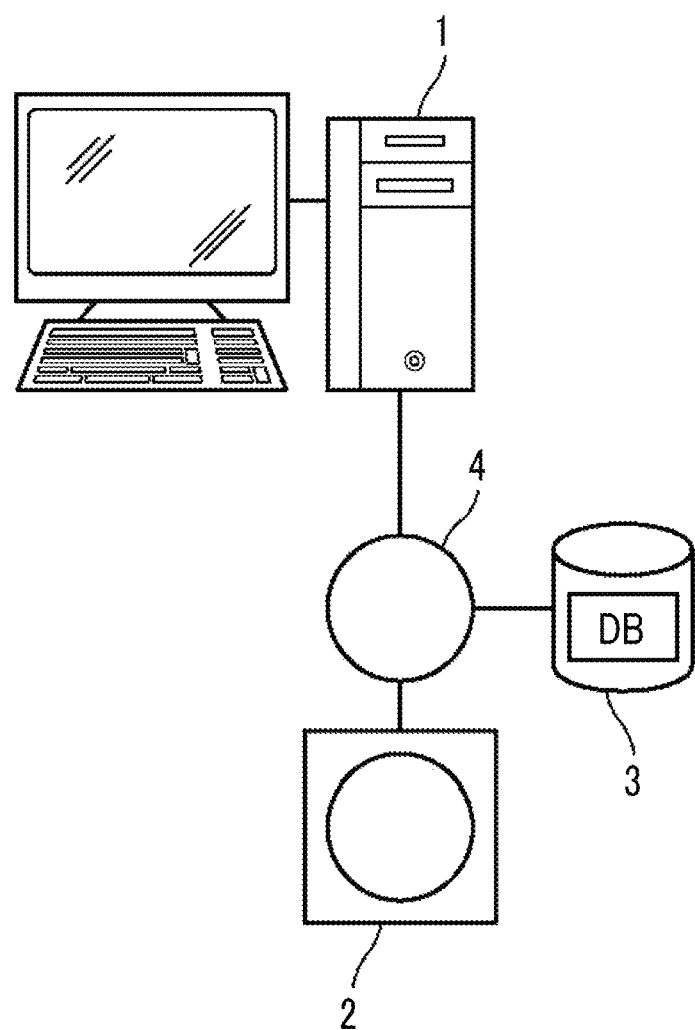
FIG. 1 is a hardware configuration diagram showing the outline of a diagnosis support system to which an image search device according to a first embodiment of the invention is applied.

Hereinafter, embodiments of the invention will be described referring to the drawings. FIG. 1 is a hardware configuration diagram showing the outline of a diagnosis support system to which an image search device according to a first embodiment of the invention is applied. As shown in FIG. 1, in the diagnosis support system, an image search device 1 according to the embodiment, a three-dimensional imaging device 2, and an image storage server 3 are connected in a communicable state by way of a network 4.

The three-dimensional imaging device 2 is a device that captures an image of a part to be a diagnosis target of a subject to generate a three-dimensional image representing the part, and is, specifically, a CT device, an MRI device, a positron emission tomography (PET) device, or the like. The three-dimensional image having a plurality of slice images generated by the three-dimensional imaging device 2 is transmitted to and stored in the image storage server 3. Note that, in the embodiment, a diagnosis target part of a patient as a subject is a lung, and the three-dimensional imaging device 2 is a CT device and generates a CT image including a chest including the lung of the subject as a three-dimensional image.

The image storage server 3 is a computer that stores and manages various kinds of data, and comprises a large capacity external storage device and database management software. The image storage server 3 performs communication with other devices through the wired or wireless network 4 and transmits and receives image data and the like. Specifically, various kinds of data including image data of the three-dimensional image generated in the three-dimensional imaging device 2 are acquired by way of the network and are stored and managed in a recording medium, such as a large capacity external storage device. Note that a storage format of image data and communication between the devices by way of the network 4 are based on a protocol, such as digital imaging and communication in medicine (DICOM). It is assumed that, in the embodiment, a case database DB in which a three-dimensional image (hereinafter, referred to as an examination image) to be a target of examination and a case image are registered is stored in the image storage server 3. The case database DB will be described below. In the embodiment, the examination image is a three-dimensional image having one or more slice images (hereinafter, referred to as examination slice images). The case image is also a three-dimensional image having one or more slice images (hereinafter, referred to as case slice images).

The image search device 1 is constituted by installing an image search program according to the embodiment of the invention on one computer. The computer may be a work station or a personal computer that is directly operated by a physician who performs diagnosis, or may be a server computer connected to the work station or the personal computer through the network. The image search program is distributed in a form of being recorded in a recording medium, such as a digital versatile disc (DVD) or a compact disc read only memory (CD-ROM), and is installed on the computer from the recording medium. Alternatively, the image search program may be stored in a storage device of a server computer connected to the network or a network storage in a form of being accessible from the outside and may be downloaded to and installed on a computer to be used by a physician.

Figure 2:
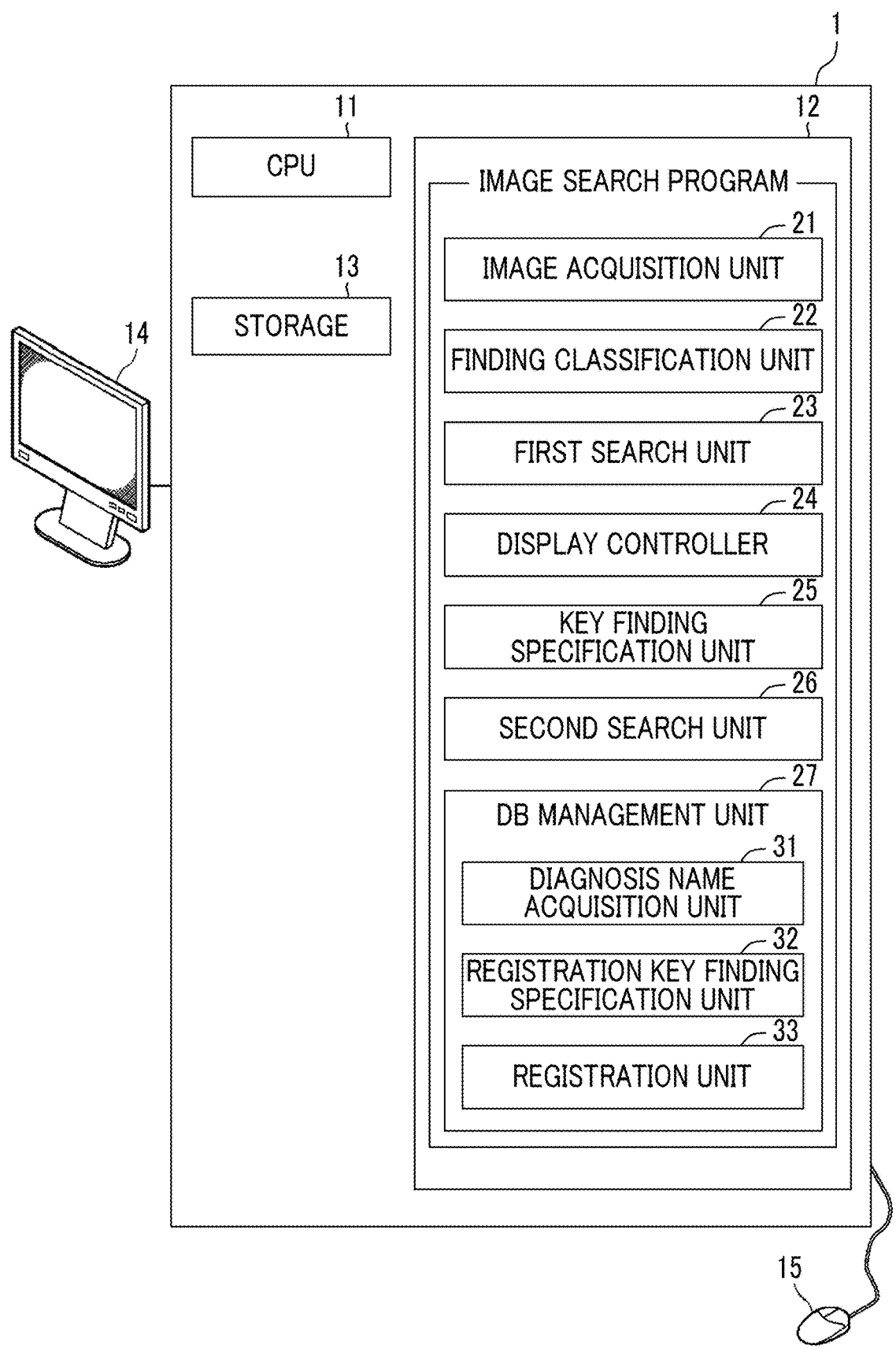
FIG. 2 is a schematic block diagram showing the configuration of the image search device according to the first embodiment.

FIG. 2 is a diagram showing the schematic configuration of the image search device according to the first embodiment of the invention that is realized by installing the image search program on the computer. As shown in FIG. 2, the image search device 1 comprises, as the configuration of a standard work station, a central processing unit (CPU) 11, a memory 12, and a storage 13. A display 14 and an input unit 15, such as a keyboard and a mouse, are connected to the image search device 1. Note that the display 14 corresponds to a display unit.

In the storage 13, various kinds of information including the examination image of the subject and information necessary for processing acquired from the image storage server 3 by way of the network 4 are stored.

In the memory 12, the image search program is stored. The image search program defines, as processing to be executed on the CPU 11, image acquisition processing for acquiring an examination image to be a target of examination, finding classification processing for classifying a target region included in the examination image into a plurality of lesion regions respectively indicating a plurality of findings to generate a finding classification result, first search processing for searching for a case image similar to the examination image as a first similar case image from a case database, in which a plurality of case images are registered, based on the finding classification result of the examination image, display control processing for displaying at least one of one or more examination slice images or the examination image on the display 14, key finding specification processing for receiving designation of a position of a key finding to at least one of the displayed one or more examination slice images or examination image to specify a position of the key finding and specifying a finding name of the key finding with the position specified, second search processing for further searching for at least one of the one or more case slice images or the case image associated with the specified position and finding name of the key finding from the first similar case image to acquire a second similar case image, and database management processing for registering the examination image in the case database. Note that the display control processing includes processing for displaying the first search result of the first search processing and the second search result of the second search processing on the display 14.

As the database management processing, diagnosis name acquisition processing for acquiring a diagnosis name of a registration target image having one or more registration target slice images to be registered in the case database, registration key finding specification processing for, with reference to a table in which a variety of diagnosis names are associated with finding names of key findings corresponding to the variety of diagnosis names, specifies a finding name of a key finding of the registration target image based on the diagnosis name of the registration target image and the finding classification result in the registration target image and specifies a position of the key finding specified in the registration target image based on the specified finding name of the key finding, and registration processing for registering the registration target image as a new case image in the case database in association with the finding classification result on the registration target image and the specified position and finding name of the key finding are defined.

Then, the CPU 11 executes the processing according to the program, whereby the computer functions as an image acquisition unit 21, a finding classification unit 22, a first search unit 23, a display controller 24, a key finding specification unit 25, a second search unit 26, and a database management unit (hereinafter, referred to as a DB management unit) 27. The DB management unit 27 functions as a diagnosis name acquisition unit 31, a registration key finding specification unit 32, and a registration unit 33. Note that, in the embodiment, although the functions of the units are executed by the image search program, the invention is not limited thereto, and the functions of the units may be executed a dedicated circuit in which a plurality of integrated circuits (ICs), processors, application specific integrated circuits (ASICs), field-programmable gate arrays (FPGAs), memories, and the like are appropriately combined. Alternatively, program commands stored in the dedicated circuit and program commands to be executed by the general CPU 11 programmed so as to use a program of the dedicated circuit may be combined.

The image acquisition unit 21 acquires an examination image V0 of a subject to be a target of examination. In the embodiment, the examination image V0 is a three-dimensional image having a plurality of examination slice images. Note that, in a case where the examination image V0 is already stored in the storage 13, the image acquisition unit 21 may acquire the examination image V0 from the storage 13.

The finding classification unit 22 classifies a lung region included in the examination image V0 into a plurality of lesion regions respectively indicating a plurality of findings. Note that the lung region corresponds to the target region. In the embodiment, the finding classification unit 22 has a discriminator constituted of a multilayer neural network subjected to deep learning so as to be able to classify a plurality of lesion regions on the lung region. In the multilayer neural network subjected to deep learning, arithmetic processing is performed on a plurality of different pieces of arithmetic result data obtained with respect to input data by a previous hierarchical layer, that is, extraction result data of a feature quantity using a variety of kernels in each layer, and additional arithmetic processing is performed on data of the feature quantity obtained in this way in subsequent processing layers, whereby it is possible to improve a recognition ratio of the feature quantity to classify input data into a plurality of classes.

Note that, in the embodiment, although an example where the multilayer neural network outputs a classification result of the lung region into a plurality of lesion regions with the examination image V0 as input has been described, a configuration may be made in which a classification result of the lung region into a plurality of lesion regions with each of a plurality of examination slice images constituting the examination image V0 as input is output.

Figure 3:
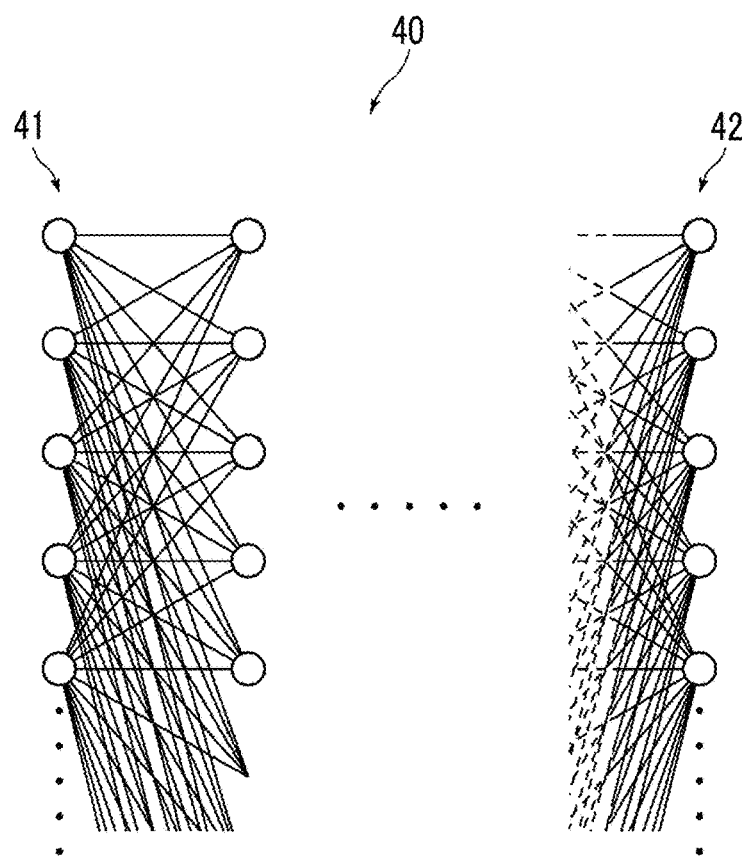
FIG. 3 is a diagram showing an example of a multilayer neural network.

FIG. 3 is a diagram showing an example of the multilayer neural network. As shown in FIG. 3, a multilayer neural network 40 has a plurality of hierarchical layers including an input layer 41 and an output layer 42. In the embodiment, learning is performed such that the lung region included in the examination image V0 is classified into 33 lesion regions respectively indicating 33 findings of normal lung, ground glass opacity (GGO) tumor nodular shadow, mixed tumor nodular shadow, solid tumor nodular shadow, frosted glass shadow, light frosted glass shadow, centrilobular frosted glass shadow, consolidation, low absorption, centrilobular emphysema, panlobular emphysema, normal pulmonary emphysema tendency, cyst, tree-in-bud appearance (TIB), small nodule (non-centrilobular), centrilobular small nodular shadow, interlobular septal thickening, bronchial wall thickening, bronchiectasis, bronchioloectasis, airbronchogram, traction bronchiectasis, cavity infiltrative shadow, cavity tumor, reticular shadow, fine reticular shadow, honeycomb lung, pleural effusion, pleural thickening, chest wall, heart, diaphragm, and blood vessel. Note that, in the following description, the names of the findings indicated by the 33 lesion regions are referred to as finding names. In the embodiment, the lesion region includes a region having a specific symptom or a specific form within the lung region. For this reason, in the embodiment, it is assumed that a region of a structure itself having a specific form, such as a heart and a diaphragm, is also included in the lesion region. Note that, in the embodiment, although the number of classifications is 33, the number of classifications may be greater or smaller than 33.

In the embodiment, the multilayer neural network 40 is made to learn the 33 lesions using a large number, millions, of pieces of teacher data. In learning, a voxel region normalized to a prescribed size (for example, 1.5 cm×1.5 cm×1.5 cm) is cut from a three-dimensional image having a known lesion, and an image of the cut voxel region is used as teacher data. Then, teacher data is input to the multilayer neural network 40, and the multilayer neural network 40 is made to output a classification result of the lesion regions. Next, the output result is compared with teacher data, and weights of links among the hierarchical layers in units (indicated by circles in FIG. 3) included in each layer of the multilayer neural network 40 are corrected from an output side toward an input side according to whether the result is a correct answer or an incorrect answer. The correction of the weights of the links is repeatedly performed using a large number of teacher data until the prescribed number of corrections is reached or until a correct answer rate of the classification result to be output becomes a prescribed correct answer rate, and learning ends.

Note that, in a case where an input image is an examination slice image, in learning of the multilayer neural network 40, a two-dimensional region normalized to a prescribed size (for example, 1.5 cm×1.5 cm) is cut from a slice image constituting a three-dimensional image having a known lesion, and an image of the cut two-dimensional region is used as teacher data.

The finding classification unit 22 extracts the lung region as the target region from the examination image V0 for classification. As a method of extracting the lung region, any method, such as a method that extracts the lung region by expressing a signal value of each pixel in the examination image V0 in the form of a histogram and subjects the lung to threshold processing or a region growing method based on a seed point representing the lung, can be used.

The finding classification unit 22 sequentially cuts the same voxel region as teacher data from the extracted lung region and inputs the voxel region to the discriminator constituted of the multilayer neural network 40 subjected to learning as described above. With this, on a center pixel of the cut region, 33 probability values to the 33 lesion regions are output. The finding classification unit 22 classifies the center pixel of the region input to the multilayer neural network 40 into a lesion region having the largest probability value among the 33 probability values to generate a finding classification result. With this, each of all pixels of the lung region included in the examination image V0 are classified into any one of the 33 lesion regions.

The finding classification unit 22 performs labeling on each classified lesion region based on the finding classification result to generate a labeled examination image V1. Specifically, the finding classification unit 22 extracts pixels in the same classification with respect to the pixels of the lung regions included in the examination image V0. Then, labeling is performed to the lesion regions having a given volume or more by assigning a different color to each lesion region and the examination image V1 is generated. Note that, in a case where labeling is performed on an examination slice image, labeling is performed to the lesion regions having a given area or more.

Figure 4:
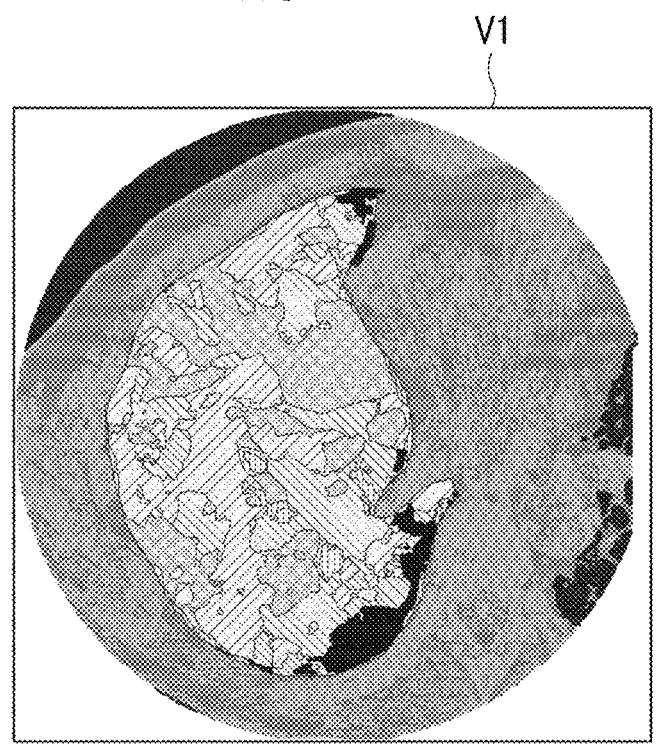
FIG. 4 is a diagram showing a labeled examination image.

FIG. 4 is a diagram showing the labeled examination image. Note that, in FIG. 4, although an examination slice image of any tomographic plane in the examination image V1 is shown, the examination slice image is represented by V1 as reference numeral. In FIG. 4, for simplification of description, only eight lesion regions of frosted glass shadow, normal shadow, bronchus, honeycomb lung, reticular shadow, consolidation, low absorption region, and cyst among the 33 lesion regions are shown. As shown in FIG. 4, in the labeled examination image V1, different colors are assigned to the separated lesion regions. In FIG. 4, the different colors are indicated by different patterns.

The first search unit 23 searches for a case image similar to the examination image V0 as a first similar case image from the case database DB based on the finding classification result of the examination image V0. First, the case database DB will be described.

In the case database DB, a plurality of case images each having one or more case slice images are registered. In detail, a finding classification result on each of a plurality of case images, a position of a key finding to be a key for specifying a diagnosis name in the finding classification result, and a finding name of the key finding are registered in association with each of a plurality of case images. In the embodiment, in a case where the examination image V0 is newly acquired, the examination image V0 is registered in the case database DB as a new case image. Note that, although an examination image is primarily registered in the case database DB, since an image that is not an examination image may be included, an image to be registered in the case database DB may be referred to as a registration target image in the following description. Hereinafter, registration of the examination image in the case database will be described.

Registration of the examination image V0 in the case database DB as a new case image is performed by the DB management unit 27. Here, the examination image V0 to be registered in the case database DB is stored in the image storage server 3 in association with an electronic medical chart created by diagnosis. In the electronic medical chart, a diagnosis result of a patient as a subject is described. In the diagnosis result, the diagnosis name of the examination image V0 is also described. In order to register the examination image V0 in the case database DB as a new case image, the diagnosis name acquisition unit 31 of the DB management unit 27 acquires the diagnosis name of the examination image V0 to be registered in the case database DB with reference to the electronic medical chart created based on the examination image V0 to be registered in the case database DB.

The registration key finding specification unit 32 of the DB management unit 27 specifies a finding name of a key finding of the examination image V0 based on the diagnosis name of the examination image V0 and the finding classification result in the examination image V0 with reference to a table in which a variety of diagnosis names are associated with finding names of key findings corresponding to a variety of diagnosis names. FIG. 5 is a diagram showing a table in which a variety of diagnosis names are associated with finding names of key findings corresponding to a variety of diagnosis names. As shown in FIG. 5, in a table LUT1, a variety of diagnosis names are associated with finding names of key findings corresponding to a variety of diagnosis names. For example, a finding name of a key finding of "TIB, bronchiectasis, traction bronchiectasis, frosted glass shadow, and honeycomb lung" is associated with a diagnosis name of "pulmonary involvement of collagen vascular disease (1) RA". The registration key finding specification unit 32 specifies the finding name of the key finding based on the diagnosis name of the examination image V0 with reference to the table LUT1. Note that, although the table LUT1 is stored in the storage 13, the table LUT1 may be stored in the image storage server 3.

Figure 6:
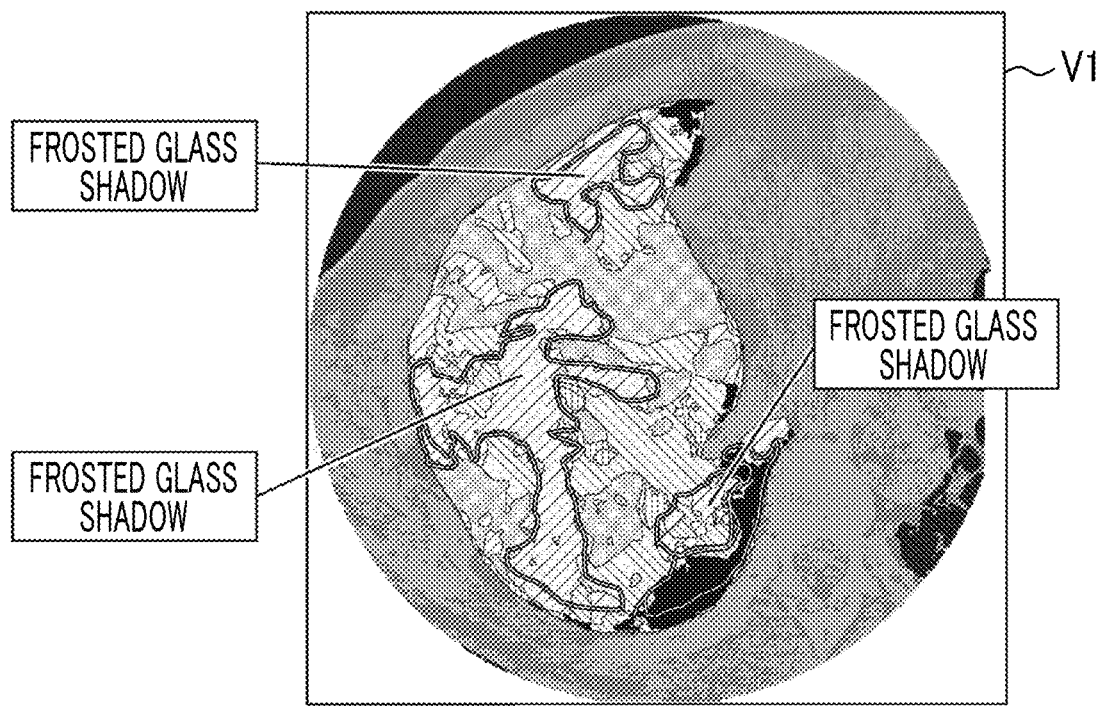
FIG. 6 is a diagram illustrating specification of a position of a key finding.

The registration key finding specification unit 32 specifies a position of the key finding specified in the examination image V0 based on the specified finding name and the finding classification result of the examination image V0. For example, in a case where the labeled examination image V1 that is generated based on the finding classification result of the examination image V0 is the image shown in FIG. 4 and the specified finding name is a frosted glass shadow, as shown in FIG. 6, positions of regions of frosted glass shadows surrounded by double lines are specified as the position of the key finding. Note that a lesion region corresponding to the key finding exists in a three-dimensional space in the examination image V0 and exists in a two-dimensional space in the examination slice image. In the embodiment, as the position of the key finding, any pixel position within the lesion region corresponding to the key finding may be used. Here, any pixel position may be all pixel positions within the lesion region or may be a pixel position representative of a region, such as the center of gravity. In the embodiment, it is assumed that the center of gravity position of the lesion region is used as the position of the key finding.

Note that, in the examination image V0, as described below, the position and the finding name of the key finding are specified by the key finding specification unit 25. For this reason, in the registration key finding specification unit 32 of the DB management unit 27, the position and the finding name of the key finding specified by the key finding specification unit 25 may be used. In this case, the registration key finding specification unit 32 can also be used as the key finding specification unit 25.

The registration unit 33 registers the examination image V0 as a new case image in the case database DB in association with the finding classification result on the examination image V0 and the specified position and finding name of the key finding. FIG. 7 is a diagram showing the configuration of the case database DB. As shown in FIG. 7, in the case database DB, a file name of a case image, such as IMG0001.dcm, a finding classification result, a file name of a labeled case image, such as IMG0001_L.dcm, a position of a specified key finding, such as (x1,y1,z1), and a finding name of a key finding, such as a frosted glass shadow, are registered. Here, although the probability values (p1 to p33) to the 33 lesion regions at the pixel positions in the examination image V0 are registered as the finding classification result, for simplification of description, the finding classification result on IMG0001.dcm only is shown. Although only one coordinate position is shown in the position of the key finding of the case database DB shown in FIG. 7, in a case where a plurality of key findings are included in the examination image V0, a plurality of coordinate positions are registered.

The first search unit 23 searches for a case image similar to the examination image V0 as a first similar case image from the case database DB, in which the case images are registered in this way, based on the finding classification result of the examination image V0. Specifically, a similarity of the finding classification result of the examination image V0 and a finding classification result of each case image registered in the case database DB is calculated, and the first similar case image is searched based on the similarity. Hereinafter, the calculation of the similarity will be described.

The first search unit 23 divides the lung region included in the examination image V0 into a plurality of subregions. In the embodiment, a lung region is divided into two regions of a center and a periphery for each lung, is divided into three regions of upper, middle, and lower regions, and is further divided into two regions of a dorsal side and a ventral side. With this, the lung region is divided into 12 subregions for each lung. Here, the center means a region in the lung close to the trachea, and the periphery means a region in the lung away from the trachea. Note that the boundary of the center and the periphery may be prescribed according to a distance from a position where the trachea is branched. The boundaries in dividing the lung regions into the three regions of the upper, middle, and lower regions may be prescribed according to a distance from an upper end of the lung. The boundary in dividing the lung region into the two regions of the dorsal side and the ventral side may be prescribed according to a direction from a position on the most ventral side or the most dorsal side of the lung, for example. Note that a method of dividing the lung region is not limited thereto, the lung region may be divided into minute subregions of a region close to and a region away from the subpleural and a region close to and a region away from the blood vessel.

The first search unit 23 calculates a feature quantity for calculating a similarity for each subregion in the examination image V0. In the embodiment, 33 average values within the subregion of the probability values on the 33 lesion regions are calculated as the feature quantity of the subregion. For this reason, the feature quantity becomes a 33-dimensional value. Similarly, the first search unit 23 divides all case images registered in the case database DB into 12 subregions for each lung and calculates 33 feature quantities for each subregion. Note that the feature quantities of each subregion on the case image are preferably calculated in advance and registered in the case database DB in achieving fast search processing.

Then, the first search unit 23 calculates the similarity of the feature quantities between the subregions of the examination image V0 and the case image. As the similarity, a correlation value between the corresponding feature quantities in the corresponding subregions of the examination image V0 and the case image can be used. As the correlation value, for example, a sum of absolute values of differential values, a sum of squares of the differential values, or the like can be used. The first search unit 23 calculates the similarity of the feature quantities for each subregion, and further calculates a weighted sum of the similarities of the feature quantities calculated for the respective subregions. The weight may be the same (for example, 1.0) with respect to the similarities on all subregions. However, the number of diseases having a lesion significantly distributed in a center portion of a lung is small except for a cancer. For this reason, in a case where a noncancerous pulmonary patient is a search target, or the like, a weight to the similarity calculated on a prescribed subregion may be made large by assigning a large weight to the similarity calculated on a subregion other than the subregion corresponding to the center, or the like to calculate the weighted sum of the similarities.

Figures 8, 9:
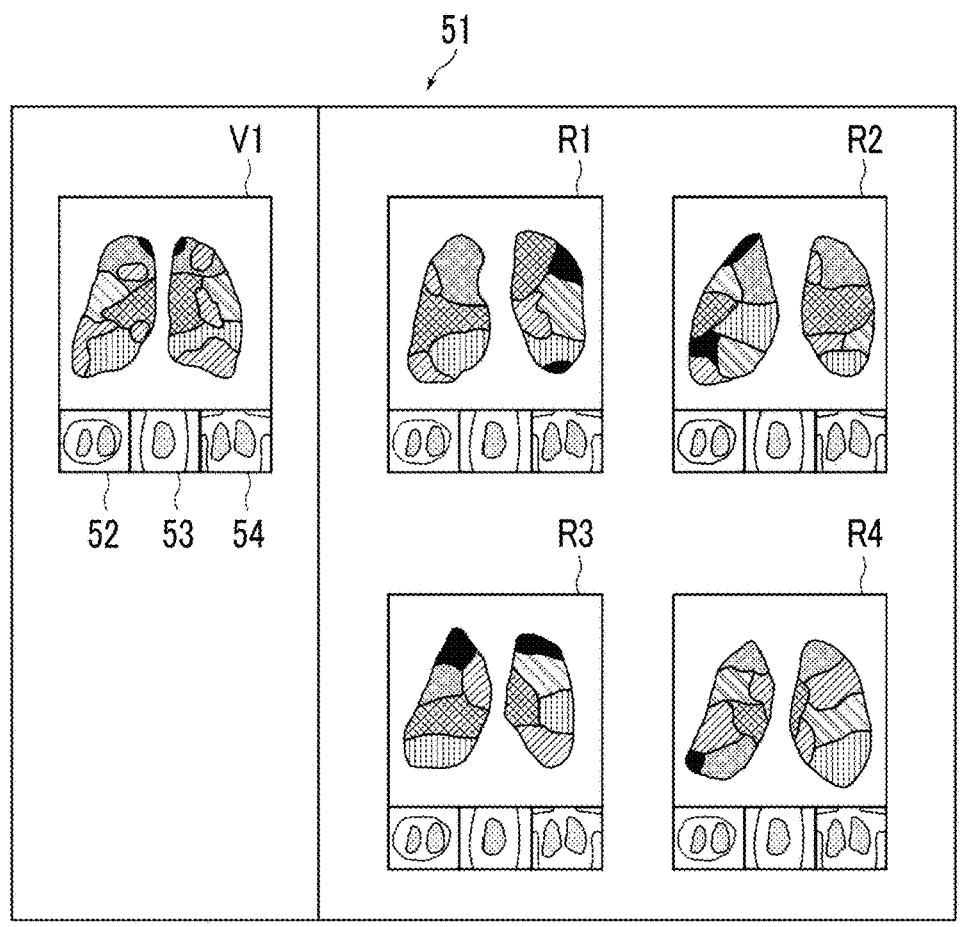
FIG. 8 is a diagram showing a first search result list.
FIG. 9 is a diagram showing a first search result.

Then, the first search unit 23 calculates the weighted sum between each of all case images registered in the case database DB and the examination image V0, and sorts the case images in a descending order of the weighted sum to create the first search result list. FIG. 8 is a diagram showing the first search result list. Then, the first search unit 23 extracts a predetermined number of case images from the highest sorting order in the first search result list as the first similar case images from the case database DB.

Note that the feature quantities calculated by the first search unit 23 are not limited to the average values of the probability values on the 33 lesion regions. For example, a ratio of the largest probability value within the subregion among the probability values on the 33 lesion regions may be used as a feature quantity. A volume of the largest probability value within the subregion among the probability values on the 33 lesion regions may be used as a feature quantity. In this case, the volume can be calculated by the number of pixels×a volume per voxel. The average values of a prescribed number (for example, three) of probability values within the subregion among the probability values on the 33 lesion regions, an average CT value, a variation value of CT values, a maximum CT value, or a minimum CT value may be used as a feature quantity.

The display controller 24 displays a search result (hereinafter, referred to as a first search result) of the first search unit 23 on the display 14. FIG. 9 is a diagram showing the first search result. As shown in FIG. 9, in a first search result 51, a labeled examination image V1 and labeled first similar case images R1 to R4 are displayed. Note that, although the four first similar case images R1 to R4 are displayed, more first similar case images may be displayed.

In FIG. 9, the examination image V1 and the first similar case images R1 to R4 are projection images projected by a prescribed projection method. Note that, in FIG. 9, although only five kinds of labeling are shown, 33 kinds of labeling are actually made. Below the examination image V1, examination slice images 52 to 54 in three cross-sections of an axial cross-section, a sagittal cross-section, and a coronal cross-section are displayed. Below the first similar case images R1 to R4, case slice image in the same three cross-sections are also displayed. Slice surfaces of the examination slice images 52 to 54 displayed below the examination image V1 and the case slice image displayed below the first similar case images R1 to R4 can be switched by an operation from the input unit 15.

The key finding specification unit 25 receives designation of a position of a key finding to the displayed examination image V0 to specify a position of the key finding and specifies a finding name of the key finding having the position designated. The specification of the position of the key finding is performed by an operator moving a cursor to the position of the key finding in the examination image V1 and performing an operation, such as a click, in the first search result 51 displayed on the display 14 according to an instruction from the input unit 15.

Figure 10:
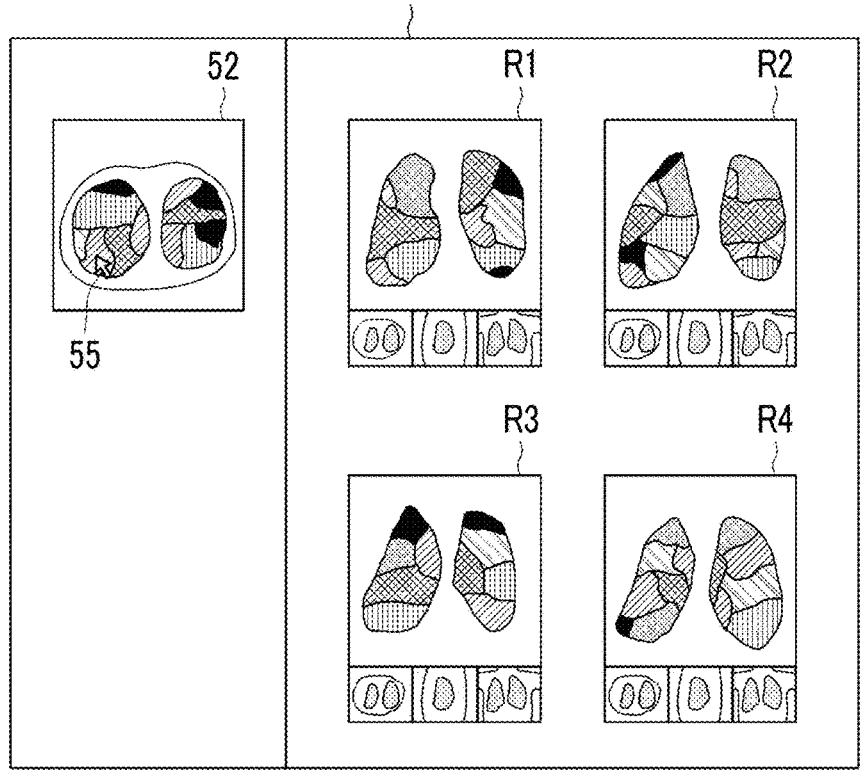
FIG. 10 is a diagram showing a first search result in which an examination slice image of an axial cross-section is displayed instead of an examination image.

Here, since the examination image V1 displayed in the first search result 51 is a projection image obtained by projecting a three-dimensional image in a two-dimensional manner, in a case where the position of the key finding in the examination image V1 is designated, it is difficult to specify a coordinate position in the examination image V0 of the position. For this reason, it is preferable that, in the first search result 51, the examination slice image is displayed instead of the examination image V1, and the position of the key finding is specified. FIG. 10 is a diagram showing the first search result in which an examination slice image of an axial cross-section is displayed instead of the examination image V1. The operator displays the examination slice image 52 of a desired slice position in the first search result 51, moves a cursor 55 to a position of a key finding on the examination slice image 52, and performs an instruction to specify the position of the key finding using the input unit 15. Since the examination slice image 52 is a two-dimensional image constituting the examination image V1 as a three-dimensional image, the position specified on the examination slice image 52 can specify a coordinate position in the three-dimensional image. Accordingly, the key finding specification unit 25 specifies the position of the key finding designated by the operator as a coordinate value on the examination image V1.

The key finding specification unit 25 specifies a finding name of the key finding specified in the examination slice image with reference to the finding classification result on the examination image V0.

The second search unit 26 further narrows down to and searches for a case image associated with the specified position and finding name of the key finding from the first similar case images to acquire a second similar case image. In the embodiment, the second search unit 26 specifies a subregion including the key finding specified in the examination image V0 in the examination image V0. Then, a similarity of pixel values of the specified subregion and a subregion in the first similar case image corresponding to the specified subregion is calculated. As the similarity, a correlation value of corresponding pixel values between the subregions of the first similar case image and the examination image V0 can be used. At this time, a weight to a pixel where the key finding is classified may be made large to calculate the correlation value. The second search unit 26 sorts the first similar case images in a descending order of the calculated similarity to create a second search result list. Then, a prescribed number of case images from the highest sorting order in the second search result list are extracted as second similar case images.

Note that the second search unit 26 may extract a case slice image including the key finding specified in the examination slice image 52 from each of the first similar case images and may calculate a similarity of the extracted case slice image and the examination slice image 52 to acquire a second similar case image.

Figure 11:
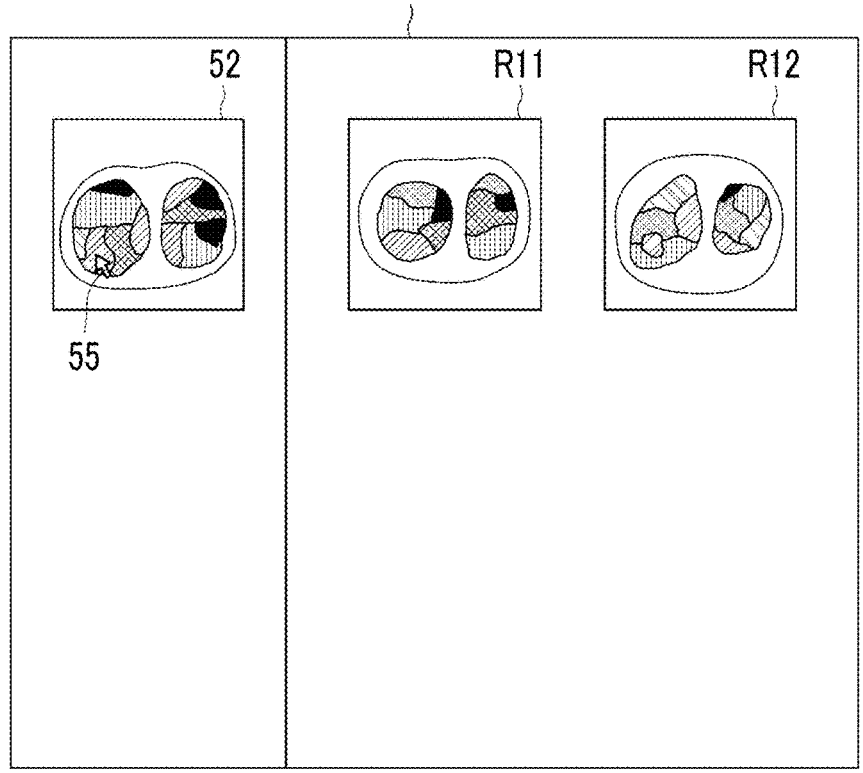
FIG. 11 is a diagram showing a second search result.

The display controller 24 displays a search result (hereinafter, referred to as a second search result) of the second search unit 26 on the display 14. FIG. 11 is a diagram showing the second search result. As shown in FIG. 11, in a second search result 57, the examination slice image 52 having the key finding designated and second similar case images R11 and R12 are displayed. Note that, in FIG. 11, although the two second similar case images R11 and R12 are displayed, more second similar case images may be displayed.

Figure 12:
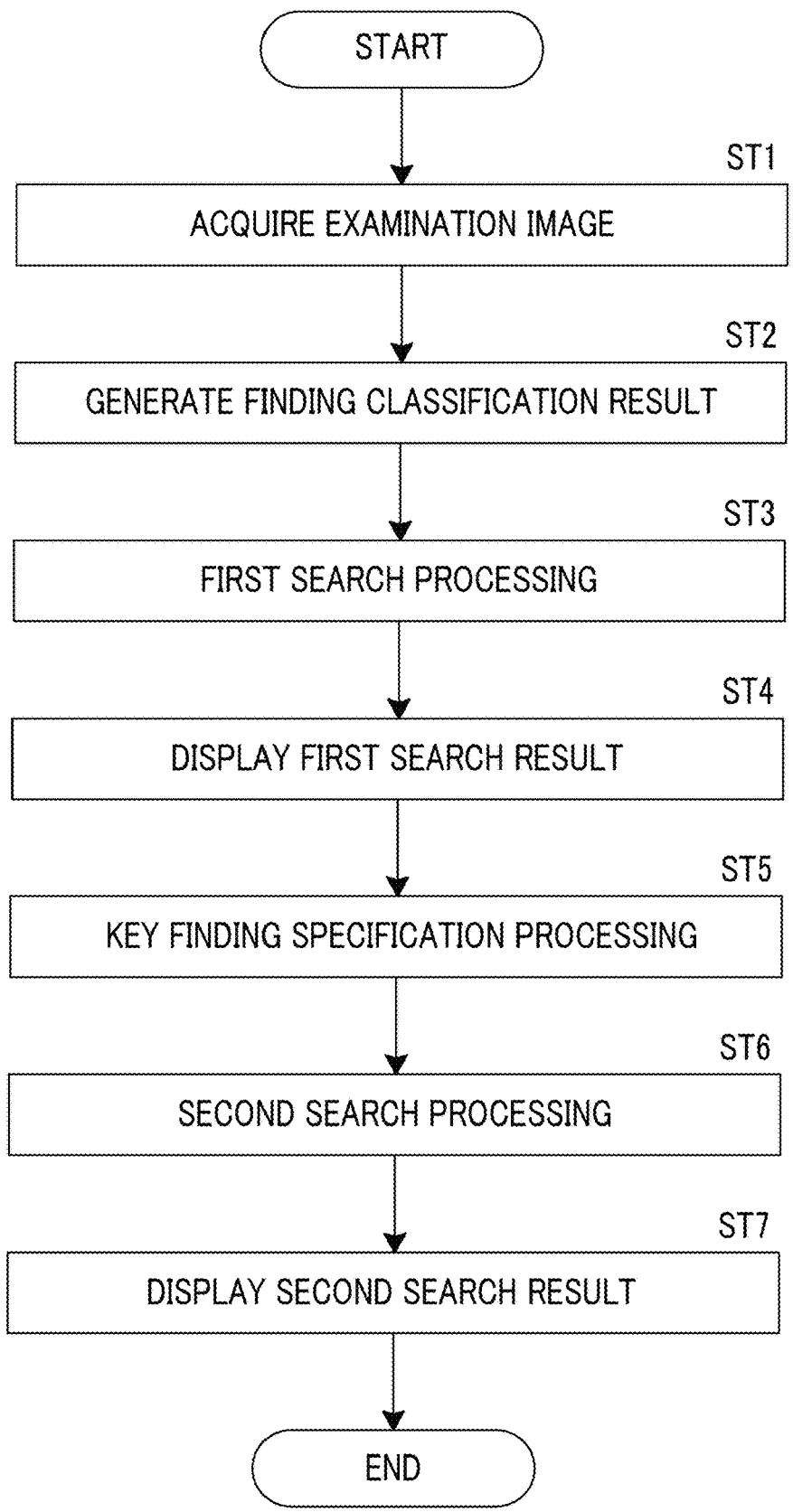
FIG. 12 is a flowchart showing processing that is performed in the first embodiment.

Next, processing that is performed in the first embodiment will be described. FIG. 12 is a flowchart showing processing that is performed in the first embodiment. First, the image acquisition unit 21 acquires the examination image V0 (Step ST1), and the finding classification unit 22 classifies the lung region included in the examination image V0 into a plurality of lesion regions respectively indicating a plurality of findings to generate the finding classification result (Step ST2). Then, the first search unit 23 searches a case image similar to the examination image V0 as a first similar case image from the case database DB based on the finding classification result of the examination image V0 (first search processing, Step ST3). Next, the display controller 24 displays the labeled examination image V1 and the first similar case images as the first search result on the display 14 (Step ST4).

In addition, the key finding specification unit 25 receives the designation of the position of the key finding to the displayed examination image V1 to specify the position of the key finding and specifies the finding name of the key finding having the position specified (key finding specification processing, Step ST5). Then, the second search unit 26 further narrows down to and searches for a case image associated with the specified position and finding name of the key finding from the first similar case images to acquire second similar case images (second search processing, Step ST6). Then, the display controller 24 displays the searched image and the second similar case images as the second search result on the display 14 (Step ST7), and ends the processing.

In this way, according to the first embodiment, it is possible to appropriately search for a case image similar to the examination image V0 based on the key finding designated to the examination image V0.

Figure 13:
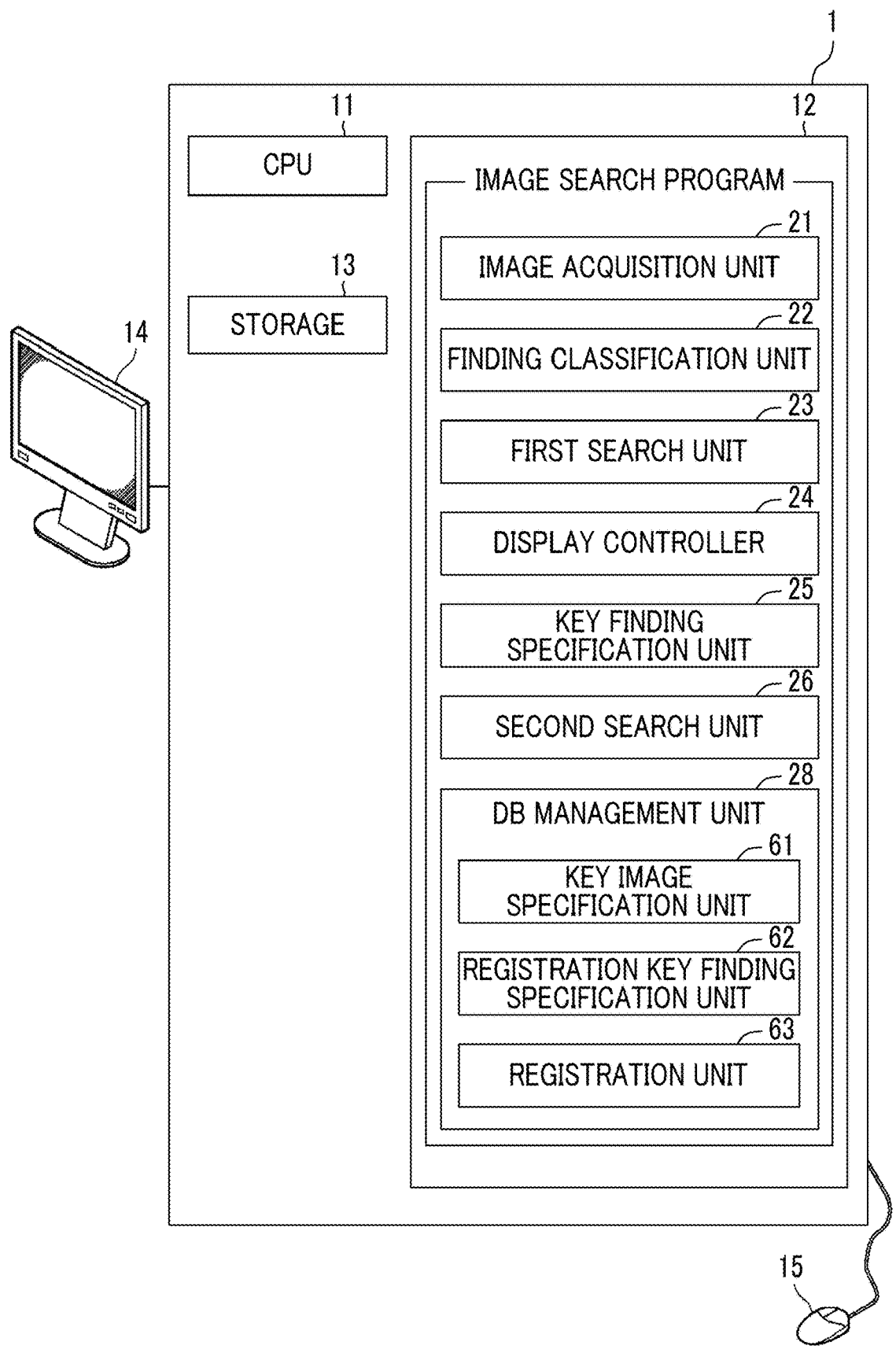
FIG. 13 is a schematic block diagram showing the configuration of an image search device according to a second embodiment.

Next, a second embodiment of the invention will be described. FIG. 13 is a diagram showing the schematic configuration of an image search device according to the second embodiment of the invention. Note that, in FIG. 13, the same configurations as those in FIG. 2 are represented by the same reference numerals, and detailed description will not be repeated. The image search device according to the second embodiment is different from the first embodiment in that the image search device comprises a DB management unit 28 different from the DB management unit 27 of the image search device according to the first embodiment.

As shown in FIG. 13, the DB management unit 28 of the image search device according to the second embodiment comprises a key image specification unit 61, a registration key finding specification unit 62, and a registration unit 63.

The key image specification unit 61 acquires a key examination slice image from the examination image V0 as a registration target image. Here, the examination image V0 to be registered in the case database DB is stored in the image storage server 3 in association with an electronic medical chart or an image interpretation report created by diagnosis. In the electronic medical chart or the image interpretation report, information for specifying an examination slice image, such as a slice position or a file name of the key examination slice image in the examination image V0, is described. Furthermore, information of the key examination slice image itself may be stored in the image storage server 3 in association with the examination image V0. Note that, as the key examination slice image, a slice image when a physician performs image diagnosis, for example, to decide a diagnosis name or a slice image including the position of the specified key finding can be used. In order to register the examination image V0 as a new case image in the case database DB, the key image specification unit 61 of the DB management unit 28 acquires the key examination slice image from the examination image V0 to be registered in the case database DB with reference to an electronic medical chart created based on the examination image V0 to be registered in the case database DB. Hereinafter, the key examination slice image is referred to as a key slice image.

The registration key finding specification unit 62 of the DB management unit 28 specifies the finding name and the position of the key finding of the examination image V0 based on a finding classification result in the key slice image.

Note that the finding classification result in the examination image V0 is already generated by the finding classification unit 22. For this reason, the registration key finding specification unit 62 refers to the finding classification result in the key slice image and specifies, as a key finding, a finding indicated by lesion regions existing equal to or greater than a prescribed threshold with respect to the lung region included in the key slice image. Note that the number of key findings may be one or plural. Furthermore, as a position of the key finding, any pixel position within the lesion region corresponding to the key finding may be used. Here, any pixel position may be all pixel positions within the lesion region or a pixel position representative of a region, such as the center of gravity. Even in the second embodiment, as in the first embodiment, it is assumed that the center of gravity position of the lesion region is used as the position of the key finding. In addition, the registration key finding specification unit 62 specifies a finding name of the key finding from the position of the key finding with reference to the finding classification result.

The registration unit 63 of the DB management unit 28 registers the finding classification result on the examination image V0, the key slice image, and the position and the finding name of the key finding specified in the key slice image as a new case image in the case database DB in association with the examination image V0. FIG. 14 is a diagram showing the configuration of the case database DB to be registered in the second embodiment. As shown in FIG. 14, in the case database DB, a file name of a case image, such as IMG0001.dcm, a finding classification result, a file name of a labeled examination image V1, such as IMG0001_L.dcm, a file name of a key slice image, such as IMG0001_010.dcm, a position of a specified key finding, such as (x1,y1,z1), and a finding name of a key finding, such as a frosted glass shadow, are registered. Note that although only one coordinate position is shown in the position of the key finding of the case database DB shown in FIG. 14, in a case where a plurality of key findings are included in the examination image V0, a plurality of coordinate positions are registered.

With the use of the case database DB in which the case images are registered in this way, in a case where a key finding is specified to an examination slice image, it is possible to efficiently perform the second search processing for searching for a second similar case image using a key slice image registered in the case database DB.

Figure 15:
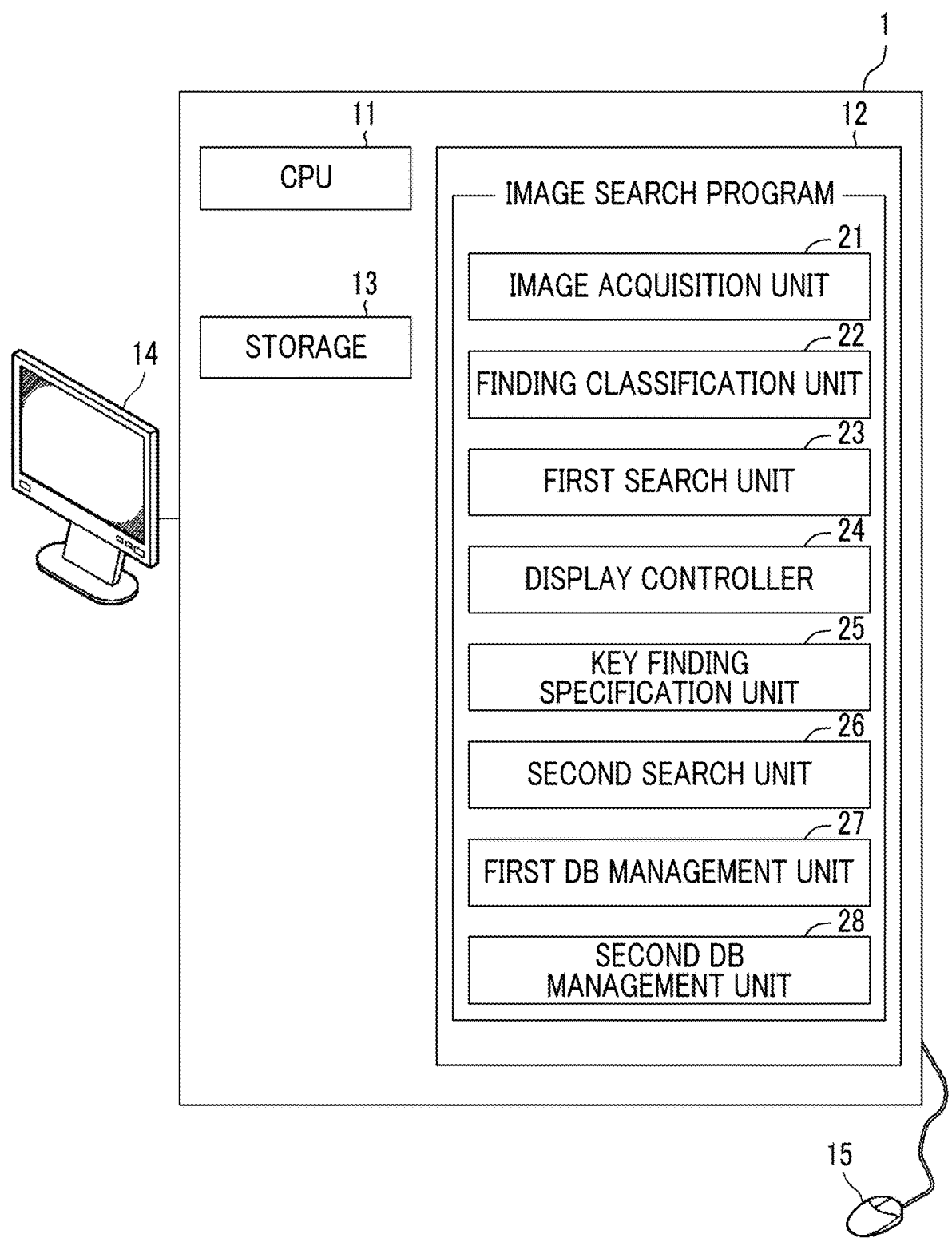
FIG. 15 is a schematic block diagram showing the configuration of an image search device according to a third embodiment.

Next, a third embodiment of the invention will be described. FIG. 15 is a diagram showing the schematic configuration of an image search device according to a third embodiment of the invention. Note that, in FIG. 15, the same configurations as those in FIG. 2 are represented by the same reference numerals, and detailed description will not be repeated. The image search device according to the third embodiment is different from the first embodiment in that the image search device comprises both of the DB management unit 27 of the image search device according to the first embodiment and the DB management unit 28 of the image search device according to the second embodiment. Note that, in the third embodiment, the DB management unit 27 according to the first embodiment is referred to as a first DB management unit 27, and the DB management unit 28 according to the second embodiment is referred to as a second DB management unit 28. Furthermore, in FIG. 15, the diagnosis name acquisition unit 31, the registration key finding specification unit 32, and the registration unit 33 of the first DB management unit 27, and the key image specification unit 61, the registration key finding specification unit 62, and the registration unit 63 of the second DB management unit 28 will be omitted. Note that the registration key finding specification unit 32 and the registration unit 33 of the first DB management unit 27 correspond to a first registration key finding specification unit and a first registration unit, respectively. Furthermore, the registration key finding specification unit 62 and the registration unit 63 of the second DB management unit 28 correspond to a second registration key finding specification unit and a second registration unit, respectively.

In the third embodiment, a new case image is registered in the case database DB by one of the first DB management unit 27 and the second DB management unit 28. Setting of using either the first DB management unit 27 or the second DB management unit 28 is performed according to an instruction of the operator from the input unit 15. Using either the first DB management unit 27 or the second DB management unit 28 may be automatically switched. For example, in a case where a table in which a variety of diagnosis names are associated with finding names of key findings corresponding to a variety of diagnosis names is broken or is not found, a case image can be registered in the case database DB using the second DB management unit 28 instead of the first DB management unit 27. Furthermore, in a case where a key slice image cannot be specified in the examination image V0, a case image can be registered in the case database DB using the first DB management unit 27 instead of the second DB management unit 28.

Note that, in the respective embodiments, although the case database DB is stored in the image storage server 3, the case database DB may be stored in the storage 13.

In the respective embodiments, although the examination image is registered in the case database DB, an image other than the examination image may be registered as a registration target image in the case database.

Hereinafter, embodiments of the invention will be described.

Embodiment 1

A database management device comprising:

a diagnosis name acquisition unit that acquires a diagnosis name of a registration target image having one or more registration target slice images to be registered in a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images;

a registration key finding specification unit that, with reference to a table in which a variety of diagnosis names are associated with finding names of key findings corresponding to the variety of diagnosis names, specifies a finding name of a key finding of the registration target image based on the diagnosis name of the registration target image and specifies a position of the key finding specified in the registration target image based on the specified finding name of the key finding and the finding classification result in the registration target image; and a registration unit that registers the registration target image as a new case image in the case database in association with the finding classification result on the registration target image and the specified position and finding name of the key finding.

Embodiment 2

A database management device comprising:
a key image acquisition unit that acquires a key registration target slice image from a registration target image having one or more registration target slice images to be registered in a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images;
a registration key finding specification unit that specifies the finding name and the position of the key finding of the examination image based on the finding classification result in the key registration target slice image; and
a registration unit that registers the registration target image as a new case image in the case database in association with the finding classification result on the registration target image and the specified position and finding name of the key finding.

Embodiment 3

A database management device comprising:
a diagnosis name acquisition unit that acquires a diagnosis name of a registration target image having one or more registration target slice images to be registered in a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images;
a first registration key finding specification unit that, with reference to a table in which a variety of diagnosis names are associated with finding names of key findings corresponding to the variety of diagnosis names, specifies a finding name of a key finding of the registration target image based on the diagnosis name of the registration target image and specifies a position of the key finding specified in the registration target image based on the specified finding name of the key finding and the finding classification result in the registration target image;
a first registration unit that registers the registration target image as a new case image in the case database in association with the finding classification result on the registration target image and the specified position and finding name of the key finding;
a key image acquisition unit that acquires a key registration target slice image from the registration target image;
a second registration key finding specification unit that specifies the finding name and the position of the key finding of the examination image based on the finding classification result in the key registration target slice image; and
a second registration unit that registers the registration target image as a new case image in the case database in association with the finding classification result on the registration target image and the specified position and finding name of the key finding.

What is claimed is:

1. An image search device comprising:
a processor configured to:
classify a target region included in an examination image having one or more examination slice images into a plurality of lesion regions respectively indicating a plurality of findings to generate a finding classification result;
search for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image;
display at least one of the one or more examination slice images or the examination image on a display unit;
receive designation of a position of a key finding to at least one of the displayed one or more examination slice images or examination image to specify a position of the key finding and specifies a finding name of the key finding having the position specified; and
further search for at least one of one or more case slice images or a case image associated with the specified position and finding name of the key finding from the first similar case image to acquire a second similar case image.

2. The image search device according to claim 1, wherein the processor is further configured to:
acquire a diagnosis name of a registration target image having one or more registration target slice images to be registered in the case database;
specify, with reference to a table in which a variety of diagnosis names are associated with finding names of key findings corresponding to the variety of diagnosis names, a finding name of a key finding of the registration target image based on the diagnosis name of the registration target image and the finding classification result in the registration target image and specifies a position of the key finding specified in the registration target image based on the specified finding name of the key finding; and
register the registration target image as a new case image in the case database in association with the finding classification result on the registration target image and the specified position and finding name of the key finding.

3. The image search device according to claim 1, wherein the processor is further configured to:
acquire a key registration target slice image from a registration target image having one or more registration target slice images to be registered in the case database;
specify the finding name and the position of the key finding of the examination image based on the finding classification result in the key registration target slice image; and
register the registration target image as a new case image in the case database in association with the finding classification result on the registration target image and the specified position and finding name of the key finding.

4. The image search device according to claim 1, wherein the processor is further configured to:
acquire a diagnosis name of a registration target image having one or more registration target slice images to be registered in the case database;

specify, with reference to a table in which a variety of diagnosis names are associated with finding names of key findings corresponding to the variety of diagnosis names, a finding name of a key finding of the registration target image based on the diagnosis name of the registration target image and specifies a position of the key finding specified in the registration target image based on the specified finding name of the key finding and the finding classification result in the registration target image;

register the registration target image as a new case image in the case database in association with the finding classification result on the registration target image and the specified position and finding name of the key finding;

acquire a key registration target slice image from the registration target image;

further specify the finding name and the position of the key finding of the examination image based on the finding classification result in the key registration target slice image; and further register the registration target image as a new case image in the case database in association with the finding classification result on the registration target image and the specified position and finding name of the key finding.

5. The image search device according to claim 1, wherein the target region included in the case image is divided into a plurality of subregions, a feature quantity relating to the lesion region is calculated on each of the plurality of subregions, and the feature quantity is registered in the case database in association with the case image, and the processor is further configured to:

divide the target region included in the examination image into a plurality of subregions corresponding to the subregions of the case image, calculate a feature quantity relating to the lesion region on each of the plurality of subregions, and search for the first similar case image from the case database based on a weighted sum of similarities of the feature quantities between the subregions of the examination image and the case image registered in the case database.

6. The image search device according to claim 1, wherein when classifying the target region included in the examination image, a discriminator subjected to deep learning is used so as to classify the plurality of findings, thereby classifying the target region into the plurality of findings with the discriminator.

7. An image search method comprising:

classifying a target region included in an examination image having one or more examination slice images into a plurality of lesion regions respectively indicating a plurality of findings to generate a finding classification result;

searching for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image;

displaying at least one of the one or more examination slice images or the examination image on a display unit;

receiving designation of a position of a key finding to at least one of the displayed one or more examination slice images or examination image to specify a position of the key finding and specifies a finding name of the key finding having the position specified; and further searching for at least one of one or more case slice images or a case image associated with the specified position and finding name of the key finding from the first similar case image to acquire a second similar case image.

8. A non-transitory computer-readable storage medium that stores an image search program that causes a computer to execute:

a procedure of classifying a target region included in an examination image having one or more examination slice images into a plurality of lesion regions respectively indicating a plurality of findings to generate a finding classification result;

a procedure of searching for a case image similar to the examination image as a first similar case image from a case database, in which a plurality of case images each having one or more a case slice images are registered and a finding classification result on each of the plurality of case images and a position and a finding name of a key finding to be a key for specifying a diagnosis name in the finding classification result are registered in association with each of the plurality of case images, based on the finding classification result of the examination image;

a procedure of displaying at least one of the one or more examination slice images or the examination image on a display unit;

a procedure of receiving designation of a position of a key finding to at least one of the displayed one or more examination slice images or examination image to specify a position of the key finding and specifies a finding name of the key finding having the position specified; and a procedure of further searching for at least one of one or more case slice images or a case image associated with the specified position and finding name of the key finding from the first similar case image to acquire a second similar case image.

* * * * *